US010386362B2

(12) United States Patent
Bahn et al.

(10) Patent No.: US 10,386,362 B2
(45) Date of Patent: Aug. 20, 2019

(54) QUANTIFYING BIOMARKERS FOR DIAGNOSING AND TREATING SCHIZOPHRENIA, BIPOLAR DISORDER OR MAJOR DEPRESSION

(71) Applicant: Cambridge Enterprise Limited, Cambridge (GB)

(72) Inventors: Sabine Bahn, Cambridge (GB); Emanuel Schwarz, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 15/416,789

(22) Filed: Jan. 26, 2017

(65) Prior Publication Data
US 2017/0212102 A1 Jul. 27, 2017

Related U.S. Application Data

(63) Continuation of application No. 13/995,838, filed as application No. PCT/GB2011/052528 on Dec. 20, 2011, now abandoned.

(30) Foreign Application Priority Data

Dec. 20, 2010 (GB) .................................. 1021498.9
Dec. 20, 2010 (GB) .................................. 1021504.4

(51) Int. Cl.
G01N 33/50 (2006.01)
G01N 33/52 (2006.01)
G01N 33/53 (2006.01)
G01N 33/68 (2006.01)
G01N 33/573 (2006.01)

(52) U.S. Cl.
CPC ......... *G01N 33/5308* (2013.01); *G01N 33/50* (2013.01); *G01N 33/52* (2013.01); *G01N 33/573* (2013.01); *G01N 33/6893* (2013.01); *G01N 33/6896* (2013.01); *G01N 2333/96494* (2013.01); *G01N 2800/28* (2013.01); *G01N 2800/2814* (2013.01); *G01N 2800/30* (2013.01); *G01N 2800/302* (2013.01); *G01N 2800/304* (2013.01)

(58) Field of Classification Search
CPC ......... G01N 33/6893; G01N 2800/304; G01N 33/6896; G01N 2800/50; G01N 2800/302; G01N 2800/30; G01N 33/50; G01N 2333/96494; G01N 2800/28; G01N 2800/2814; G01N 33/52; G01N 33/5308; G01N 33/573
See application file for complete search history.

(56) References Cited

U.S. PATENT DOCUMENTS

| | | |
|---|---|---|
| 2004/0053292 A1 | 3/2004 | Tschopp et al. |
| 2006/0099593 A1 | 5/2006 | Nawa et al. |
| 2007/0003981 A1 | 1/2007 | Chandler et al. |
| 2009/0175827 A1 | 7/2009 | Byrom et al. |
| 2009/0176257 A1 | 7/2009 | Bahn |
| 2011/0165554 A1 | 7/2011 | Levin et al. |
| 2014/0200150 A1 | 7/2014 | Bahn et al. |

FOREIGN PATENT DOCUMENTS

| | | |
|---|---|---|
| CN | 1654957 A | 8/2005 |
| WO | WO 2008/090319 A2 | 7/2008 |
| WO | WO 2009/077763 A1 | 6/2009 |
| WO | WO 2012/085557 A2 | 6/2012 |

OTHER PUBLICATIONS

Babity et al., "A novel seizure-induced synaptotagmin gene identified by differential display", Proc. Natl. Acad. Sci. USA, vol. 94. No. 6, pp. 2638-2641 (1997).
Blashki et al., "Managing schizophrenia in general practice", Australian Family Physician, vol. 33, No. 4, pp. 221-227 (2004).
Bock, "Immunoglobulins, prealbumin, transferrin, albumin, and alpha2-macroglobulin in cerebrospinal fluid and serum in schizophrenic patients", Birth Defects, vol. 14, No. 5, pp. 283-295 (1978).
Ferguson et al., "Synaptotagmin IV: biochemistry, genetics, behavior, and possible links to human psychiatric disease", Mol. Neurobiol., vol. 23, No. 2/3. pp. 173-185 (2001).
Fuchikami et al., "Decreased expression of matrix metalloprotease-9 and its cleavage of proBDNF is involved in the enhanced susceptibility to depression by early adversities", Society for Neuroscience, Presentation Abstract, Program No. 658.11/FF31, 2 pages (2008).
Ganzinelli et al., "Autoantibodies from schizophrenia patients induce cerebral cox-1/iNOS mRNA expression with NO/PGE2/MMP-3 production", Int. J. Neuropsychopharmacol., vol. 13, No. 3, pp. 293-303 (2010).
Geddes et al., "Atypical antipsychotics in the treatment of schizophrenia: systematic overview and meta-regression analysis", Biomedical J., vol. 321, vol. 7273, pp. 1371-1376 (2000).
Glavan and Zivin, "Differential expression of striatal synaptotagmin mRNA isoforms in hemiparkinsonian rats", Neuroscience, vol. 135, pp. 545-554 (2005).
Huang et al., "Disease biomarkers in cerebrospinal fluid of patients with first-onset psychosis", PLOS Medicine, vol. 3, No. 11, pp. 2145-2158 (2006).
International Search Report from PCT Patent Application No. PCT/GB2011/052528 dated Aug. 22, 2012, application now published as International Publication No. WO2012/085557 on Jun. 28, 2012.
Jiang et al., "Proteomic analysis of the cerebrospinal fluid of patients with schizophrenia", Amino Acids, vol. 25, No. 1, pp. 49-57 (2003).
Kucukali et al., "Do schizophrenia and bipolar disorders share a common disease susceptibility variant at the MMP3 gene?", Prog. Neuro-Psych. Biol. Psych., vol. 33, No. 3, pp. 557-561 (2009).

(Continued)

*Primary Examiner* — Gregory S Emch
(74) *Attorney, Agent, or Firm* — McDermott Will & Emery LLP; Judy M. Mohr; Wen Li

(57) ABSTRACT

The invention relates to a method of differentially diagnosing schizophrenia, bipolar disorder and major depressive disorder.

16 Claims, 2 Drawing Sheets

(56) References Cited

OTHER PUBLICATIONS

Maes et al., "Acute phase proteins in schizophrenia, mania and major depression: modulation by psychotropic drugs", Psychiatry Res., vol. 66, No. 1, pp. 1-11 (1997).

Nnadi et al., "Individualizing antipsychotic drug therapy in schizophrenia: the promise of pharmacogenetics", Curr. Psychology Rep., vol. 9, No. 4, pp. 313-318 (2007).

Pepe et al., "Lipoprotein(a) in the cerebrospinal fluid of neurological patients with blood-cerebrospinal fluid barrier dysfunction", Clinical Chemistry, vol. 52, No. 11, pp. 2043-2048 (2006).

Randox Clinical Chemistry Multisera website, Online article retrieved from the internet Oct. 6, 2013 http://web.archive.org/web/20080915173112/http://www.randox.com/clinical%20chemistry.php, 8 pages, published Jun. 2008.

Schmitt et al., "Increased serum S100B in elderly, chronic schizophrenic patients: negative correleation with deficit symptons", Schizophrenia Research, vol. 80, Issue 2-3, pp. 305-313 (2005).

Schwarz et al., "Validation of a blood-based laboratory test to aid in the confirmation of a diagnosis of schizophrenia", Biomarker Insights, vol. 5, pp. 39-47 (2010).

Sudhof, "Synaptotagmins: why so many?", J. Biol. Chem., vol. 277, pp. 7629-7632 (2002).

Yang et al., "Altered levels of acute phase proteins in the plasma of patients with schizophrenia", Anal. Chem., vol. 78, pp. 3571-3576 (2006).

Yokota et al., "Polymorphic 33-bp repeats with promoter-like activity in synaptotagmin 11 gene", DNA Research, vol. 10, No. 6, pp. 287-289 (2003).

| Added analyte | | classification accuracy rate |
|---|---|---|
| 1 | Cortisol | 0.74022 |
| 2 | Alpha.1.Antitrypsin | 0.74715 |
| 3 | IL16 | 0.75872 |
| 4 | MMP.2 | 0.76337 |
| 5 | EGF.R | 0.77024 |
| 6 | MMP.3 | 0.77717 |
| 7 | Alpha.2.Macroglobulin | 0.78399 |
| 8 | SHBG | 0.79086 |
| 9 | IGF.1 | 0.79318 |
| 10 | BLC..B.Lymphocyte.Chemoattractant. | 0.79323 |
| 11 | EGF | 0.79556 |
| 12 | IL.1alpha | 0.79789 |
| 13 | Insulin | 0.79789 |
| 14 | Complement.3 | 0.79789 |
| 15 | Erythropoietin | 0.80021 |
| 16 | FABP | 0.80021 |
| 17 | ACTH..Adrenocorticitropic.Hormone. | 0.80021 |
| 18 | Growth.Hormone | 0.80021 |
| 19 | HB.EGF | 0.80021 |
| 20 | AgRP..Agouti.related.Protein | 0.80021 |
| 21 | IgA | 0.80021 |

# QUANTIFYING BIOMARKERS FOR DIAGNOSING AND TREATING SCHIZOPHRENIA, BIPOLAR DISORDER OR MAJOR DEPRESSION

CROSS REFERENCE TO RELATED APPLICATIONS

This application is a continuation of U.S. application Ser. No. 13/995,838, which is a U.S. National Stage of International Patent Application No. PCT/GB2011/052528, filed Dec. 20, 2011, which claims the benefit of GB Application No. 1021498.9, filed Dec. 20, 2010 and GB Application No. 1021504.4, filed Dec. 20, 2010, the contents of which are incorporated herein by reference in their entirety.

FIELD OF THE INVENTION

The invention relates to a method of differentially diagnosing schizophrenia, bipolar disorder and major depressive disorder.

BACKGROUND OF THE INVENTION

Schizophrenia

Schizophrenia is a psychiatric diagnosis that describes a mental disorder characterized by abnormalities in the perception or expression of reality. It most commonly manifests as auditory hallucinations, paranoid or bizarre delusions, or disorganized speech and thinking with significant social or occupational dysfunction. Onset of symptoms typically occurs in young adulthood, with approximately 0.4-0.6% of the population affected. Diagnosis is based on the patient's self-reported experiences and observed behavior. No laboratory test for schizophrenia currently exists.

Studies suggest that genetics, early environment, neurobiology, psychological and social processes are important contributory factors; some recreational and prescription drugs appear to cause or worsen symptoms. Current psychiatric research is focused on the role of neurobiology, but no single organic cause has been found. Due to the many possible combinations of symptoms, there is debate about whether the diagnosis represents a single disorder or a number of discrete syndromes.

The disorder is thought to mainly affect cognition, but it also usually contributes to chronic problems with behavior and emotion. People with schizophrenia are likely to have additional (comorbid) conditions, including major depression and anxiety disorders; the lifetime occurrence of substance abuse is around 40%. Social problems, such as long-term unemployment, poverty and homelessness, are common. Furthermore, the average life expectancy of people with the disorder is 10 to 12 years less than those without, due to increased physical health problems and a higher suicide rate.

An important utility of biomarkers for psychotic disorders is their response to medication. Administration of antipsychotics remains a subjective process, relying solely on the experience of clinicians. Furthermore, the development of antipsychotic drugs has been based on chance findings often with little relation to the background driving the observations.

Schizophrenia is treated primarily with antipsychotic medications which are also referred to as neuroleptic drugs or neuroleptics. Newer antipsychotic agents such as clozapine, olanzapine, quetiapine or risperidone are thought to be more effective in improving negative symptoms of psychotic disorders than older medication like Chlorpromazine. Furthermore, they induce less extrapyramidal side effects (EPS) which are movement disorders resulting from antipsychotic treatment.

The history of neuroleptics dates back to the late 19th century. The flourishing dye industry catalyzed development of new chemicals that lay the background to modern day atypical antipsychotics. Developments in anti-malaria, anti-histamine and anaesthetic compounds also produced various neuroleptics. The common phenomenon to all these processes is a fundamental lack of understanding of the biological mechanisms and pathways that these drugs affect, apart from the observation that they prominently block D2 receptors in the striatum.

Bipolar Disorder

Bipolar disorder is a psychiatric disease that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. Such individuals also experience a decreased quality of life. These episodes are usually separated by periods of "normal" mood, but in some individuals, depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum.

Bipolar I disorder is characterised by manic episodes; the "high" of the manic-depressive cycle. Generally, this manic period is followed by a period of depression, although some bipolar I individuals may not experience a major depressive episode. Mixed states, where both manic or hypomanic symptoms and depressive symptoms occur at the same time, also occur frequently with bipolar I patients (for example, depression with the racing thoughts of mania). Also, dysphoric mania is common and is mania characterised by anger and irritability.

Bipolar II disorder is characterised by major depressive episodes alternating with episodes of hypomania, a milder form of mania. Hypomanic episodes can be a less disruptive form of mania and may be characterised by low-level, non-psychotic symptoms of mania, such as increased energy or a more elevated mood than usual. It may not affect an individual's ability to function on a day to day basis. The criteria for hypomania differ from those for mania only by their shorter duration (at least 4 days instead of 1 week) and milder severity (no marked impairment of functioning, hospitalisation or psychotic features).

If the depressive and manic symptoms last for two years and do not meet the criteria for a major depressive or a manic episode then the diagnosis is classified as a cyclothymic disorder, which is a less severe form of bipolar affective disorder. Cyclothymic disorder is diagnosed over the course of two years and is characterised by frequent short periods of hypomania and depressive symptoms separated by periods of stability.

Rapid cycling occurs when an individual's mood fluctuates from depression to hypomania or mania in rapid succession with little or no periods of stability in between. One is said to experience rapid cycling when one has had four or more episodes in a given year that meet criteria for major depressive, manic, mixed or hypomanic episodes. Some people who rapid cycle can experience monthly, weekly or even daily shifts in polarity (sometimes called ultra rapid cycling).

To date, no empirical diagnostic tests are available, making diagnosis a subjective evaluation which often leads to misdiagnosis and delay in accurate treatment. When symptoms of mania, depression, mixed mood or hypomania are caused directly by a medical disorder, such as thyroid disease or a stroke, the current diagnosis is Mood Disorder Due to a General Medical Condition.

In a manic mood brought about through an antidepressant, ECT or through an individual using street drugs, the diagnosis is Substance-Induced Mood Disorder, with Manic Features.

Diagnosis of bipolar disorders has been used to categorise manic episodes which occur as a result of taking an antidepressant medication, rather than occurring spontaneously. Confusingly, it has also been used in instances where an individual experiences hypomania or cyclothymia (i.e., less severe mania) without major depression.

Major Depressive Disorder

Major depressive disorder is a mental disorder characterized by a pervasive low mood, low self-esteem, and loss of interest or pleasure in normally enjoyable activities. The term "major depressive disorder" (which is also known as clinical depression, major depression, unipolar depression, or unipolar disorder) was selected by the American Psychiatric Association for this symptom cluster under mood disorders in the 1980 version of the *Diagnostic and Statistical Manual of Mental Disorders* (DSM-III) classification, and has become widely used since.

The general term depression is often used to describe the disorder, but as it is also used to describe a depressed mood, more precise terminology is preferred in clinical and research use. Major depression is a disabling condition which adversely affects a person's family, work or school life, sleeping and eating habits, and general health. In the United States, approximately 3.4% of people with major depression commit suicide, and up to 60% of all people who commit suicide have depression or another mood disorder.

The diagnosis of major depressive disorder is based on the patient's self-reported experiences, behaviour reported by relatives or friends, and a mental status exam. There is no laboratory test for major depression, although physicians generally request tests for physical conditions that may cause similar symptoms. The most common time of onset is between the ages of 30 and 40 years, with a later peak between 50 and 60 years. Major depression is reported about twice as frequently in women as in men, although men are at higher risk for suicide.

Most patients are treated in the community with antidepressant medication and some with psychotherapy or counseling. Hospitalization may be necessary in cases with associated self-neglect or a significant risk of harm to self or others. A minority are treated with electroconvulsive therapy (ECT), under a short-acting general anaesthetic.

The course of the disorder varies widely, from one episode lasting months to a lifelong disorder with recurrent major depressive episodes. Depressed individuals have shorter life expectancies than those without depression, in part because of greater susceptibility to medical illnesses. Current and former patients may be stigmatized.

The understanding of the nature and causes of depression has evolved over the centuries, though many aspects of depression remain incompletely understood and are the subject of discussion and research.

In view of the related symptoms, it is becoming increasingly difficult for medical practitioners to effectively diagnose one psychiatric disorder from another, particular for schizophrenia, bipolar disorder and major depressive disorder. There is therefore a pressing need for objective molecular readouts that can differentially diagnose psychiatric disorders such as schizophrenia, bipolar disorder and major depressive disorder.

SUMMARY OF THE INVENTION

According to a first aspect of the invention, there is provided the use of one or more analytes selected from: MMP 3, Alpha 1 Antitrypsin, ACTH (Adrenocorticotropic Hormone), AgRP (Agouti related Protein), Apolipoprotein A1, Apolipoprotein H, AXL, Betacellulin, BLC (B Lymphocyte Chemoattractant), BDNF (Brain Derived Neurotrophic Factor), Complement 3, Cancer Antigen 125, Carcinoembryonic Antigen, CgA (Chromogranin A), Creatine Kinase MB, Cortisol, CTGF (Connective Tissue Growth Factor), EGF R, Endothelin 1, EN RAGE, Eotaxin, Epiregulin, Erythropoietin, Factor VII, Fas, Fas Ligand, Ferritin, FGF basic, Fibrinogen, FSH (Follicle Stimulating Hormone), GM CSF, GST, Haptoglobin, HB EGF, HGF (Hepatocyte growth factor), IFN gamma, IGF-1, Ig A, Ig M, IL 10, IL 12p'70, IL 13, IL 15, IL 16, IL 18, IL 1 alpha, IL 1beta, IL 1ra, IL 2, IL 3, IL 4, IL 5, IL 7, Leptin, LH (Luteinizing Hormone), Lipoprotein a, Lymphotactin, M CSF, MDC, MIP 1 alpha, MIP 3 alpha, MIP 1 beta, Myoglobin, NrCAM, PAI 1, Prostatic Acid Phosphatase, PAPP A, PDGF, Progesterone, Prolactin, Prostate Specific Antigen Free, PARC, Peptide YY, RANTES, Resistin, S100b, Serum Amyloid P, SGOT, SHBG, SOD, sRAGE, Tamm-Horsfall Protein (THP), Thyroxine Binding Globulin, Testosterone, Tissue Factor, TECK, TIMP 1, TNF RII, TRAIL R3, Thyroid Stimulating Hormone, TSP 1, VCAM 1, von Willebrand Factor, as a biomarker for the differential diagnosis of schizophrenia, bipolar disorder and major depressive disorder or predisposition thereto.

According to a second aspect of the invention, there is provided a method of differentially diagnosing or monitoring schizophrenia, bipolar disorder and major depressive disorder, or predisposition thereto, comprising detecting and/or quantifying, in a sample from a test subject, the analyte biomarkers defined herein. There is also provided a method of diagnosing or monitoring major depressive disorder, or predisposition thereto, comprising detecting and/or quantifying, in a sample from a test subject, the analyte biomarkers defined herein.

According to a third aspect of the invention, there is provided a method of differentially diagnosing schizophrenia, bipolar disorder and major depressive disorder or predisposition thereto in an individual thereto, comprising:
(a) obtaining a biological sample from an individual;
(b) quantifying the amounts of one or more analyte biomarkers as defined hereinbefore;
(c) comparing the amounts of the analyte biomarkers in the biological sample with the amounts present in control biological samples obtained from subjects having schizophrenia, bipolar disorder and major depressive disorder to provide differential diagnosis of schizophrenia, bipolar disorder and major depressive disorder, or predisposition thereto. There is also provided a method of diagnosing major depressive disorder, or predisposition thereto, over psychotic disorders, such as schizophrenia, in an individual, comprising:

(a) obtaining a biological sample from an individual;
(b) quantifying the amounts of the analyte biomarkers as defined herein;
(c) comparing the amounts of the analyte biomarkers in the biological sample with the amounts present in a normal control biological sample from a normal subject, such that a difference in the level of the analyte biomarkers in the biological sample is indicative of major depressive disorder, or predisposition thereto, over psychotic disorders, such as schizophrenia.

According to a fourth aspect of the invention, there is provided a method of monitoring efficacy of a therapy in a subject having, suspected of having, or of being predisposed to major depressive disorder, comprising detecting and/or quantifying, in a sample from said subject, one or more of the analyte biomarkers defined herein.

According to a fifth aspect of the invention, there is provided a method of determining the efficacy of therapy for major depressive disorder in an individual subject comprising:
(a) obtaining a biological sample from an individual;
(b) quantifying the amounts of the analyte biomarkers as defined herein;
(c) comparing the amounts of the analyte biomarkers in the biological sample with the amounts present in a sample obtained from the individual on a previous occasion, such that a difference in the level of the analyte biomarkers in the biological sample is indicative of a beneficial effect of the therapy.

According to a sixth aspect of the invention, there is provided a method of monitoring efficacy of a therapy in a subject having, suspected of having, or of being predisposed to major depressive disorder, comprising detecting and/or quantifying, in a sample from said subject, two or more of the second analyte biomarkers defined herein.

A further aspect of the invention provides ligands, such as naturally occurring or chemically synthesised compounds, capable of specific binding to the analyte biomarker. A ligand according to the invention may comprise a peptide, an antibody or a fragment thereof, or an aptamer or oligonucleotide, capable of specific binding to the analyte biomarker. The antibody can be a monoclonal antibody or a fragment thereof capable of specific binding to the analyte biomarker. A ligand according to the invention may be labelled with a detectable marker, such as a luminescent, fluorescent or radioactive marker; alternatively or additionally a ligand according to the invention may be labelled with an affinity tag, e.g., a biotin, avidin, streptavidin or His (e.g., hexa-His) tag.

A biosensor according to the invention may comprise the analyte biomarker or a structural/shape mimic thereof capable of specific binding to an antibody against the analyte biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the analyte. In these uses, the detection and/or quantification can be performed on a biological sample such as from the group consisting of CSF, whole blood, blood serum, plasma, urine, saliva, or other bodily fluid, breath, e.g., as condensed breath, or an extract or purification therefrom, or dilution thereof.

Diagnostic or monitoring kits are provided for performing methods of the invention. Such kits will suitably comprise a ligand according to the invention, for detection and/or quantification of the analyte biomarker, and/or a biosensor, and/or an array as described herein, optionally together with instructions for use of the kit.

A further aspect of the invention is a kit for differentially diagnosing schizophrenia, bipolar disorder and major depressive disorder, or predisposition thereto, comprising a biosensor capable of detecting and/or quantifying one or more of the analyte biomarkers as defined herein. There is also provided a kit for monitoring or diagnosing major depressive disorder, or predisposition thereto, over psychotic disorders, such as schizophrenia, comprising a biosensor capable of detecting and/or quantifying one or more of the biomarkers as defined herein.

Biomarkers for differentially diagnosing schizophrenia, bipolar disorder and major depressive disorder are essential targets for discovery of novel targets and drug molecules that retard or halt progression of these disorders. As the level of the analyte biomarker is indicative of disorder and of drug response, the biomarker is useful for identification of novel therapeutic compounds in in vitro and/or in vivo assays. Biomarkers of the invention can be employed in methods for screening for compounds that modulate the activity of the analyte.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the analyte in a subject, comprising administering a test substance to a subject animal and detecting and/or quantifying the level of the analyte biomarker present in a test sample from the subject.

DETAILED DESCRIPTION OF THE INVENTION

Figure 1:
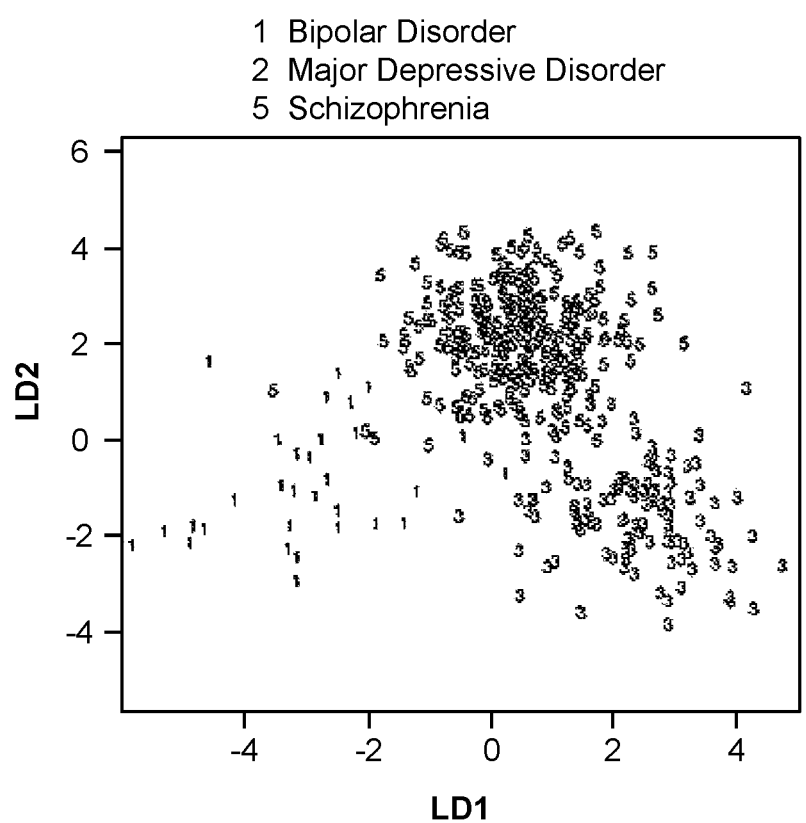
FIG. 1 describes the results obtained when data from the analytes of the invention were inputted into an algorithm to differentially diagnose schizophrenia, bipolar disorder and major depressive disorder patients.

According to a first aspect of the invention, there is provided the use of one or more analytes selected from: MMP 3, Alpha 1 Antitrypsin, ACTH (Adrenocorticotropic Hormone), AgRP (Agouti related Protein), Apolipoprotein A1, Apolipoprotein H, AXL, Betacellulin, BLC (B Lymphocyte Chemoattractant), BDNF (Brain Derived Neurotrophic Factor), Complement 3, Cancer Antigen 125, Carcinoembryonic Antigen, CgA (Chromogranin A), Creatine Kinase MB, Cortisol, CTGF (Connective Tissue Growth Factor), EGF R, Endothelin 1, EN RAGE, Eotaxin, Epiregulin, Erythropoietin, Factor VII, Fas, Fas Ligand, Ferritin, FGF basic, Fibrinogen, FSH (Follicle Stimulating Hormone), GM CSF, GST, Haptoglobin, HB EGF, HGF (Hepatocyte growth factor), IFN gamma, IGF-1, Ig A, Ig M, IL 10, IL 12p70, IL 13, IL 15, IL 16, IL 18, IL 1alpha, IL 1 beta, IL 1ra, IL 2, IL 3, IL 4, IL 5, IL 7, Leptin, LH (Luteinizing Hormone), Lipoprotein a, Lymphotactin, M CSF, MDC, MIP 1alpha, MIP 3 alpha, MIP 1beta, Myoglobin, NrCAM, PAI 1, Prostatic Acid Phosphatase, PAPP A, PDGF, Progesterone, Prolactin, Prostate Specific Antigen Free, PARC, Peptide YY, RANTES, Resistin, S100b, Serum Amyloid P, SGOT, SHBG, SOD, sRAGE, Tamm-Horsfall Protein (THP), Thyroxine Binding Globulin, Testosterone, Tissue Factor, TECK, TIMP 1, TNF RII, TRAIL R3, Thyroid Stimulating Hormone, TSP 1, VCAM 1, von Willebrand Factor, as a biomarker for the differential diagnosis of schizophrenia, bipolar disorder and major depressive disorder or predisposition thereto.

In one embodiment, the analytes are selected from one or more of: MMP 3, Alpha 1 Antitrypsin, BLC (B Lymphocyte Chemoattractant), Cortisol, Haptoglobin, IL 16, IL 10, EGF R, Complement 3 or S100b.

In one embodiment, the analytes are selected from one or more of: MMP 3, IL 10, BDNF (Brain Derived Neurotrophic Factor), Serum Amyloid P, Betacellulin, CgA (Chromogranin A), IGF-1, S100b, IL 1ra or IL 18.

In a further embodiment, the analyte is selected from MMP-3. Data is presented herein which demonstrates that the levels of MMP-3 were found to be increased in patients with major depressive disorder when compared with schizophrenia patients and increased in patients with major depressive disorder when compared with healthy controls. Thus, MMP-3 not only provides a sensitive diagnostic marker for major depressive disorder but surprisingly also provides a differential diagnostic marker for major depressive disorder over schizophrenia.

According to a first particular aspect of the invention which may be mentioned, there is provided the use of one or more analytes selected from: Alpha 1 Antitrypsin, ACTH (Adrenocorticotropic Hormone), AgRP (Agouti related Protein), Apolipoprotein A1, Apolipoprotein H, AXL, Betacellulin, BLC (B Lymphocyte Chemoattractant), BDNF (Brain Derived Neurotrophic Factor), Complement 3, Cancer Antigen 125, Carcinoembryonic Antigen, CgA (Chromogranin A), Creatine Kinase MB, Cortisol, CTGF (Connective Tissue Growth Factor), EGF R, Endothelin 1, EN RAGE, Eotaxin, Epiregulin, Erythropoietin, Factor VII, Fas, Fas Ligand, Ferritin, FGF basic, Fibrinogen, FSH (Follicle Stimulating Hormone), GM CSF, GST, Haptoglobin, HB EGF, HGF (Hepatocyte growth factor), IFN gamma, Ig A, Ig M, IL 10, IL 12p'70, IL 13, IL 15, IL 16, IL 1alpha, IL 1beta, IL 1ra, IL 2, IL 3, IL 4, IL 5, IL 7, Leptin, LH (Luteinizing Hormone), Lipoprotein a, Lymphotactin, M CSF, MDC, MIP 1alpha, MIP 1beta, MMP 3, Myoglobin, NrCAM, PAI 1, Prostatic Acid Phosphatase, PAPP A, PDGF, Prolactin, Prostate Specific Antigen Free, PARC, Peptide YY, RANTES, Resistin, S100b, Serum Amyloid P, SGOT, SHBG, SOD, Thyroxine Binding Globulin, Testosterone, Tissue Factor, TECK, TIMP 1, TNF RII, TRAIL R3, Thyroid Stimulating Hormone, TSP 1, VCAM 1, von Willebrand Factor, as a biomarker for the differential diagnosis of schizophrenia, bipolar disorder and major depressive disorder or predisposition thereto.

It will be appreciated that the term "differential diagnosis" refers to the positive diagnosis of a first psychiatric disorder from that of a second psychiatric disorder. For example, in the present invention the psychiatric disorders are selected from schizophrenia, bipolar disorder and major depressive disorder.

Thus, in one embodiment the differential diagnosis comprises diagnosis of at least one of the following conditions:

(i) schizophrenia from bipolar disorder;
(ii) schizophrenia from major depressive disorder;
(iii) schizophrenia from bipolar disorder and major depressive disorder;
(iv) bipolar disorder from schizophrenia;
(v) bipolar disorder from major depressive disorder;
(vi) bipolar disorder from schizophrenia and major depressive disorder;
(vii) major depressive disorder from schizophrenia;
(viii) major depressive disorder from bipolar disorder; or
(ix) major depressive disorder from schizophrenia and bipolar disorder.

In a further embodiment, the differential diagnosis comprises diagnosis of at least one of the following conditions:

(iii) schizophrenia from normal controls and bipolar disorder and major depressive disorder;
(vi) bipolar disorder from normal controls and schizophrenia and major depressive disorder; or
(ix) major depressive disorder from normal controls and schizophrenia and bipolar disorder.

According to a second particular aspect of the invention which may be mentioned, there is provided the use of one or more analytes selected from: Tamm-Horsfall Protein (THP), MIP-3 alpha Betacellulin, MMP-3, sRAGE, IL-1ra, Progesterone, IL-10, Brain Derived Neurotrophic Factor (BDNF), Serum Amyloid P, Chromogranin A, Creatine Kinase MB, IGF-1, S100b and IL-18, as a biomarker for the differential diagnosis of major depressive disorder, or predisposition thereto, over psychotic disorders, such as schizophrenia.

Data is presented herein which shows that the levels of the 15 analytes of the second particular aspect of the invention were found to be significantly altered between the major depressive disorder group and the schizophrenia group (Table 3). The invention therefore provides a specific and sensitive diagnosis for major depressive disorder which may be differentiated from psychotic disorders such as schizophrenia.

In one embodiment of the second particular aspect of the invention, the analyte is selected from MMP-3, Betacellulin, MIP-3 alpha and Tamm-Horsfall Protein (THP). Data is presented herein which demonstrates that the biomarkers of this embodiment were found to be increased in patients with major depressive disorder when compared with schizophrenia patients (for example the data shows a fold change of >1).

In a further embodiment of the second particular aspect of the invention, the analyte is selected from MMP-3. Data is presented herein which demonstrates that the levels of MMP-3 were found to be increased in patients with major depressive disorder when compared with schizophrenia patients and increased in patients with major depressive disorder when compared with healthy controls. Thus, MMP-3 not only provides a sensitive diagnostic marker for major depressive disorder but surprisingly also provides a differential diagnostic marker for major depressive disorder over schizophrenia. Thus, according to a further aspect of the invention there is provided the use of MMP-3 as a biomarker for major depressive disorder, or predisposition thereto. In one embodiment of this aspect of the invention, the use additionally comprises one or more analytes selected from sRAGE, Betacellulin, MIP-3 alpha and Tamm-Horsfall Protein (THP).

In one embodiment of the second particular aspect of the invention, the analyte is selected from sRAGE. Data is presented herein which demonstrates that the biomarker of this embodiment was found to be decreased in patients with major depressive disorder when compared with schizophrenia patients (for example the data shows a fold change of <1).

In one embodiment of the second particular aspect of the invention, the analyte is selected from: IL-1ra, Progesterone, IL-10, Serum Amyloid P, Chromogranin A, Creatine Kinase MB, S100b and IL-18. Data is presented herein which demonstrates that the biomarkers of this embodiment were found to be increased in patients with major depressive disorder when compared with schizophrenia patients.

In a further embodiment of the second particular aspect of the invention, the analyte is selected from IL-1ra. Data is presented herein which demonstrates that the levels of IL-1ra were found to be increased in patients with major depressive disorder when compared with schizophrenia patients and increased in patients with major depressive disorder when compared with healthy controls. Thus, IL-1ra not only provides a sensitive diagnostic marker for major depressive disorder but surprisingly also provides a differential diagnostic marker for major depressive disorder over schizophrenia. Thus, according to a further aspect of the invention, there is provided the use of IL-1ra in combination with one or more analytes selected from MMP-3, sRAGE, Betacellulin, MIP-3 alpha, Tamm-Horsfall Protein (THP), Progesterone, IL-10, Brain Derived Neurotrophic Factor (BDNF), Serum Amyloid P, Chromogranin A, Creatine Kinase MB, IGF-1, S100b and IL-18, as a biomarker for major depressive disorder, or predisposition thereto. In one embodiment of this aspect of the invention, the analyte is selected from MMP-3. According to a further aspect of the invention, there is provided the use of MMP-3 and IL-1ra as a specific panel of analyte biomarkers for the differential diagnosis of major depressive disorder, or predisposition thereto over psychotic disorders, such as schizophrenia. In one embodiment of this aspect of the invention, the panel additionally comprises one or more analytes selected from sRAGE, Betacellulin, MIP-3 alpha, Tamm-Horsfall Protein (THP), Progesterone, IL-10, Brain Derived Neurotrophic Factor (BDNF), Serum Amyloid P, Chromogranin A, Creatine Kinase MB, IGF-1, S100b and IL-18.

In an alternative embodiment of the second particular aspect of the invention, the analyte is selected from: Brain Derived Neurotrophic Factor (BDNF) and IGF-1. Data is presented herein which demonstrates that the biomarkers of this embodiment were found to be decreased in patients with major depressive disorder when compared with schizophrenia patients.

According to a further aspect of the invention, there is provided the use of MMP-3, sRAGE, Betacellulin, MIP-3 alpha, Tamm-Horsfall Protein (THP), IL-1ra, Progesterone, IL-10, Brain Derived Neurotrophic Factor (BDNF), Serum Amyloid P, Chromogranin A, Creatine Kinase MB, IGF-1, S100b and IL-18 as a specific panel of analyte biomarkers for major depressive disorder, or predisposition thereto. Data is presented herein which demonstrates that this specific panel of biomarkers were found to be altered in patients with major depressive disorder when compared with schizophrenia patients. Thus, according to a further aspect of the invention, there is provided the use of MMP-3, sRAGE, Betacellulin, MIP-3 alpha, Tamm-Horsfall Protein (THP), IL-1ra, Progesterone, IL-10, Brain Derived Neurotrophic Factor (BDNF), Serum Amyloid P, Chromogranin A, Creatine Kinase MB, IGF-1, S100b and IL-18 as a specific panel of analyte biomarkers for the differential diagnosis of major depressive disorder, or predisposition thereto over psychotic disorders, such as schizophrenia.

According to a further aspect of the invention, there is provided the use of MMP-3, Betacellulin, MIP-3 alpha, Tamm-Horsfall Protein (THP), IL-1ra, Progesterone, IL-10, Serum Amyloid P, Chromogranin A, Creatine Kinase MB, S100b and IL-18 as a specific panel of analyte biomarkers for major depressive disorder, or predisposition thereto. Data is presented herein which demonstrates that this specific panel of biomarkers were found to be increased in patients with major depressive disorder when compared with schizophrenia patients. Thus, according to a further aspect of the invention, there is provided the use of MMP-3, Betacellulin, MIP-3 alpha, Tamm-Horsfall Protein (THP), IL-1ra, Progesterone, IL-10, Serum Amyloid P, Chromogranin A, Creatine Kinase MB, S100b and IL-18 as a specific panel of analyte biomarkers for the differential diagnosis of major depressive disorder, or predisposition thereto over psychotic disorders, such as schizophrenia.

According to a further aspect of the invention, there is provided the use of Brain Derived Neurotrophic Factor (BDNF), sRAGE and IGF-1 as a specific panel of analyte biomarkers for major depressive disorder, or predisposition thereto. Data is presented herein which demonstrates that this specific panel of biomarkers were found to be decreased in patients with major depressive disorder when compared with schizophrenia patients. Thus, according to a further aspect of the invention, there is provided the use of Brain Derived Neurotrophic Factor (BDNF), sRAGE and IGF-1 as a specific panel of analyte biomarkers for the differential diagnosis of major depressive disorder, or predisposition thereto over psychotic disorders, such as schizophrenia.

The term "biomarker" means a distinctive biological or biologically derived indicator of a process, event, or condition. Peptide biomarkers can be used in methods of diagnosis, e.g., clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

Figure 2:
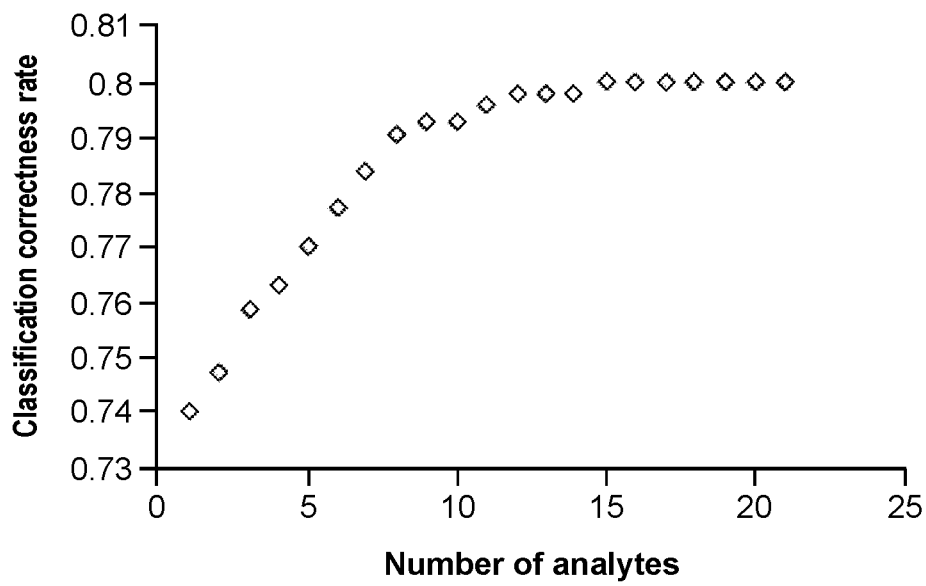
FIG. 2 describes a statistical analysis which indicates the optimum number of biomarkers for a panel of biomarkers.

In one embodiment of the invention, the number of analytes comprise any one of the following numbers of analytes: 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more. Results of a statistical analysis with a known algorithm are shown in FIG. 2 wherein it can be seen that the most predictive analyte achieved a classification accuracy rate of 0.74022. The results of additional analyte biomarkers were then added to the algorithm to improve statistical performance until it can no longer be improved. It can be seen from the results shown in FIG. 2 that a panel of at least 5 biomarkers achieved a correctness rate of greater than 0.77 and that the performance did not improve for a panel of biomarkers in excess of 15. The results of the analysis shown in FIG. 2 therefore demonstrate that the optimal panel size for the analyte biomarkers of the invention is between 5 and 15. Thus, in one embodiment, there is provided a panel of biomarkers which comprises between 5 and 15 of the analytes hereinbefore defined.

According to a further aspect of the invention, there is provided a method of differentially diagnosing schizophrenia, bipolar disorder and major depressive disorder or predisposition thereto in an individual thereto, comprising:
 (a) obtaining a biological sample from an individual;
 (b) quantifying the amounts of one or more analyte biomarkers as defined hereinbefore;

(c) comparing the amounts of the analyte biomarkers in the biological sample with the amounts present in control biological samples obtained from subjects having schizophrenia, bipolar disorder and major depressive disorder to provide differential diagnosis of schizophrenia, bipolar disorder and major depressive disorder, or predisposition thereto.

According to a further aspect of the invention, there is provided a method of diagnosing major depressive disorder, or predisposition thereto, in an individual thereto comprising
(a) obtaining a biological sample from an individual;
(b) quantifying the amounts of a panel of analyte biomarkers in the biological sample, wherein the panel of analyte biomarkers comprises Brain Derived Neurotrophic Factor (BDNF), sRAGE and IGF-1; and
(c) comparing the amounts of the panel of analyte biomarkers in the biological sample with the amounts present in a normal control biological sample from a normal subject, wherein a lower level of the panel of analyte biomarkers in the biological sample is indicative of major depressive disorder, or predisposition thereto.

In one embodiment, the lower level is a <1 fold difference relative to the control sample, such as a fold difference of 0.9, 0.8, 0.7, 0.6, 0.5, 0.4, 0.3, 0.2, 0.1, 0.05, 0.01 or any ranges therebetween. In one embodiment, the lower level is between 0.1 and 0.9 fold difference relative to the control sample, such as between 0.5 and 0.9.

According to a further aspect of the invention, there is provided a method of diagnosing major depressive disorder, or predisposition thereto, in an individual thereto comprising
(a) obtaining a biological sample from an individual;
(b) quantifying the amounts of a panel of analyte biomarkers in the biological sample, wherein the panel of analyte biomarkers comprises MMP-3, Betacellulin, MIP-3 alpha, Tamm-Horsfall Protein (THP), IL-1ra, Progesterone, IL-10, Serum Amyloid P, Chromogranin A, Creatine Kinase MB, S100b and IL-18; and
(c) comparing the amounts of the panel of analyte biomarkers in the biological sample with the amounts present in a normal control biological sample from a normal subject, wherein a higher level of the panel of analyte biomarkers in the biological sample is indicative of major depressive disorder, or predisposition thereto.

In one embodiment, the higher level is a >1 fold difference relative to the control sample, such as a fold difference of 1.1, 1.2, 1.3, 1.4, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges therebetween. In one embodiment, the higher level is between 1 and 10 fold difference relative to the control sample, such as between 1.2 and 2.5.

As used herein, the term "biosensor" means anything capable of detecting the presence of the biomarker. Examples of biosensors are described herein.

In one embodiment, one or more of the biomarkers defined hereinbefore may be replaced by a molecule, or a measurable fragment of the molecule, found upstream or downstream of the biomarker in a biological pathway.

Biosensors according to the invention may comprise a ligand or ligands, as described herein, capable of specific binding to the analyte biomarker. Such biosensors are useful in detecting and/or quantifying an analyte of the invention.

Diagnostic kits for the differential diagnosis of schizophrenia, bipolar disorder and major depressive disorder or predisposition thereto are described herein. In one embodiment, the kits additionally contain a biosensor capable of detecting and/or quantifying a peptide biomarker.

In methods of diagnosing according to the invention, detecting and/or quantifying the peptide biomarker in a biological sample from a test subject may be performed on two or more occasions. Comparisons may be made between the level of biomarker in samples taken on two or more occasions. Assessment of any change in the level of the peptide biomarker in samples taken on two or more occasions may be performed. Modulation of the analyte biomarker level is useful as an indicator of the state of schizophrenia, bipolar disorder and major depressive disorder or predisposition thereto. An increase in the level of the biomarker over time is indicative of onset or progression, i.e., worsening of this disorder, whereas a decrease in the level of the analyte biomarker indicates amelioration or remission of the disorder, or vice versa.

A method of diagnosis according to the invention may comprise quantifying the analyte biomarker in a test biological sample from a test subject and comparing the level of the analyte present in said test sample with one or more controls.

The control used in a method of the invention can be one or more control(s) selected from the group consisting of: the level in a sample from a subject with schizophrenia, bipolar disorder and major depressive disorder, or a diagnosed predisposition thereto; schizophrenia, bipolar disorder or major depressive disorder biomarker analyte level, or schizophrenia, bipolar disorder and major depressive disorder biomarker analyte range.

In one embodiment, there is provided a method of diagnosing major depressive disorder, or predisposition thereto, which comprises:
(a) quantifying the amount of the peptide biomarker in a test biological sample; and
(b) comparing the amount of said peptide in said test sample with the amount present in a normal control biological sample from a normal subject.

For biomarkers which are increased in patients with major depressive disorder, a higher level of the peptide biomarker in the test sample relative to the level in the normal control is indicative of the presence of major depressive disorder, or predisposition thereto; an equivalent or lower level of the peptide in the test sample relative to the normal control is indicative of absence of major depressive disorder and/or absence of a predisposition thereto. For biomarkers which are decreased in patients with major depressive disorder, a lower level of the peptide biomarker in the test sample relative to the level in the normal control is indicative of the presence of major depressive disorder, or predisposition thereto; an equivalent or lower level of the peptide in the test sample relative to the normal control is indicative of absence of major depressive disorder and/or absence of a predisposition thereto.

The term "diagnosis" as used herein encompasses identification, confirmation, and/or characterisation of schizophrenia, bipolar disorder and major depressive disorder, or predisposition thereto. By predisposition it is meant that a subject does not currently present with the disorder, but is liable to be affected by the disorder in time. Methods of diagnosis according to the invention are useful to confirm the existence of a disorder, or predisposition thereto. Methods of diagnosis are also useful in methods for assessment of clinical screening, prognosis, choice of therapy, evaluation of therapeutic benefit, i.e., for drug screening and drug development.

Efficient diagnosis methods provide very powerful "patient solutions" with the potential for improved prognosis, by establishing the correct diagnosis, allowing rapid identification of the most appropriate treatment (thus lessening unnecessary exposure to harmful drug side effects), reducing "down-time" and relapse rates.

Also provided is a method of monitoring efficacy of a therapy for major depressive disorder in a subject having such a disorder, suspected of having such a disorder, or of being predisposed thereto, comprising detecting and/or quantifying the peptide present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g., prior to commencement of therapy, and/or from the same test subject at an earlier stage of therapy. The method may comprise detecting a change in the level of the biomarker(s) in test samples taken on different occasions.

The invention provides a method for monitoring efficacy of therapy for major depressive disorder in a subject, comprising:
(a) quantifying the amount of the peptide biomarker; and
(b) comparing the amount of said peptide in said test sample with the amount present in one or more control(s) and/or one or more previous test sample(s) taken at an earlier time from the same test subject.

For biomarkers which are increased in patients with major depressive disorder, a decrease in the level of the peptide biomarker in the test sample relative to the level in a previous test sample taken earlier from the same test subject is indicative of a beneficial effect, e.g., stabilisation or improvement, of said therapy on the disorder, suspected disorder or predisposition thereto. For biomarkers which are decreased in patients with major depressive disorder, an increase in the level of the peptide biomarker in the test sample relative to the level in a previous test sample taken earlier from the same test subject is indicative of a beneficial effect, e.g., stabilisation or improvement, of said therapy on the disorder, suspected disorder or predisposition thereto.

Methods for monitoring efficacy of a therapy can be used to monitor the therapeutic effectiveness of existing therapies and new therapies in human subjects and in non-human animals (e.g., in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an anti-depressant therapy. Samples can be taken at intervals over the remaining life, or a part thereof, of a subject.

The term "detecting" as used herein means confirming the presence of the analyte biomarker present in the sample. Quantifying the amount of the analyte biomarker present in a sample may include determining the concentration of the analyte biomarker present in the sample. Detecting and/or quantifying may be performed directly on the sample, or indirectly on an extract therefrom, or on a dilution thereof.

In alternative aspects of the invention, the presence of the analyte biomarker is assessed by detecting and/or quantifying antibody or fragments thereof capable of specific binding to the biomarker that are generated by the subject's body in response to the analyte and thus are present in a biological sample from a subject having schizophrenia, bipolar disorder or major depressive disorder or a predisposition thereto.

Detecting and/or quantifying can be performed by any method suitable to identify the presence and/or amount of a specific analyte in a biological sample from a patient or a purification or extract of a biological sample or a dilution thereof. In methods of the invention, quantifying may be performed by measuring the concentration of the analyte biomarker in the sample or samples. Biological samples that may be tested in a method of the invention include cerebrospinal fluid (CSF), whole blood, blood serum, plasma, urine, saliva, or other bodily fluid (stool, tear fluid, synovial fluid, sputum), breath, e.g., as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

Detection and/or quantification of analyte biomarkers may be performed by detection of the analyte biomarker or of a fragment thereof, e.g., a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length.

The biomarker may be directly detected, e.g., by SELDI or MALDI-TOF. Alternatively, the biomarker may be detected directly or indirectly via interaction with a ligand or ligands such as an antibody or a biomarker-binding fragment thereof, or other peptide, or ligand, e.g., aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g., high pressure liquid chromatography (HPLC) or low pressure liquid chromatography (LPLC)), thin-layer chromatography, NMR (nuclear magnetic resonance) spectroscopy could also be used.

Methods of diagnosing according to the invention may comprise analysing a sample of cerebrospinal fluid (CSF) by SELDI TOF or MALDI TOF to detect the presence or level of the analyte biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the analyte biomarkers may be performed using an immunological method, involving an antibody, or a fragment thereof capable of specific binding to the analyte biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g., using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes that are too small to precipitate. However, these complexes will scatter incident light and this can be measured using a nephelometer. The antigen, i.e., biomarker, concentration can be determined within minutes of the reaction.

Radioimmunoassay (RIA) methods employ radioactive isotopes such as 1125 to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radioimmunoassays (RIA). These methods use an enzyme to label either the antibody or target antigen. The sensitivity of EIA approaches that for RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of peptide biomarkers of the invention.

The Biotin-Avidin or Biotin-Streptavidin systems are generic labelling systems that can be adapted for use in immunological methods of the invention. One binding partner (hapten, antigen, ligand, aptamer, antibody, enzyme, etc.) is labelled with biotin and the other partner (surface, e.g., well, bead, sensor, etc.) is labelled with avidin or streptavidin. This is conventional technology for immunoassays, gene probe assays and (bio)sensors, but is an indirect immobilisation route rather than a direct one. For example a biotinylated ligand (e.g., antibody or aptamer) specific for an analyte biomarker of the invention may be immobilised on an avidin or streptavidin surface, the immobilised ligand may then be exposed to a sample containing or suspected of containing the analyte biomarker in order to detect and/or quantify an analyte biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, Fab fragments and F(ab')$_2$ fragments, fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers appropriate diagnostic tools such as biosensors can be developed, accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g., hologram) or acoustic technologies. Using such biosensors, it is possible to detect the target biomarker(s) at the anticipated concentrations found in biological samples.

Thus, according to a further aspect of the invention there is provided an apparatus for differentially diagnosing schizophrenia, bipolar disorder and major depressive disorder or predisposition thereto which comprises a biosensor, microanalytical, microengineered, microseparation and/or immunochromatography system configured to detect and/or quantify any of the biomarkers defined herein.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g., in the ward, outpatients' department, surgery, home, field and workplace.

Biosensors to detect one or more biomarkers of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the one or more biomarkers of the invention.

Methods involving detection and/or quantification of one or more analyte biomarkers of the invention can be performed on bench-top instruments, or can be incorporated onto disposable, diagnostic or monitoring platforms that can be used in a non-laboratory environment, e.g., in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example, a non-human primate, horse, cow, pig, goat, sheep, dog, cat, fish, rodent, e.g., guinea pig, rat or mouse; insect (e.g., *Drosophila*), amphibian (e.g., *Xenopus*) or *C. elegans*.

The test substance can be a known chemical or pharmaceutical substance, such as, but not limited to, an antidepressive disorder therapeutic; or the test substance can be novel synthetic or natural chemical entity, or a combination of two or more of the aforesaid substances.

There is provided a method of identifying a substance capable of promoting or suppressing the generation of the analyte biomarker in a subject, comprising exposing a test cell to a test substance and monitoring the level of the analyte biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g., from *Xenopus*), *C. elegans* cell or is a cell of human, non-human primate, equine, bovine, porcine, caprine, ovine, canine, feline, piscine, rodent or murine origin.

In methods for identifying substances of potential therapeutic use, non-human animals or cells can be used that are capable of expressing the peptide.

Screening methods also encompass a method of identifying a ligand capable of binding to the analyte biomarker according to the invention, comprising incubating a test substance in the presence of the analyte biomarker in conditions appropriate for binding, and detecting and/or quantifying binding of the analyte to said test substance.

High-throughput screening technologies based on the biomarker, uses and methods of the invention, e.g., configured in an array format, are suitable to monitor biomarker signatures for the identification of potentially useful therapeutic compounds, e.g., ligands such as natural compounds, synthetic chemical compounds (e.g., from combinatorial libraries), peptides, monoclonal or polyclonal antibodies or fragments thereof, which may be capable of binding the biomarker.

Methods of the invention can be performed in array format, e.g., on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g., a ligand, identified or identifiable by an identification or screening method or use of the invention. Such substances may be capable of inhibiting, directly or indirectly, the activity of the analyte biomarker, or of suppressing generation of the analyte biomarker.

The term "substances" includes substances that do not directly bind the peptide biomarker and directly modulate a function, but instead indirectly modulate a function of the analyte biomarker. Ligands are also included in the term substances; ligands of the invention (e.g., a natural or synthetic chemical compound, peptide, aptamer, oligonucleotide, antibody or antibody fragment) are capable of binding, suitably specific binding, to the analyte.

The invention further provides a substance according to the invention for use in the treatment of schizophrenia, bipolar disorder or major depressive disorder or predisposition thereto. For example, the invention provides a substance according to the invention for use in the treatment of major depressive disorder, or predisposition thereto.

Also provided is the use of a substance according to the invention in the treatment of schizophrenia, bipolar disorder or major depressive disorder, or predisposition thereto. For example, also provided is the use of a substance according to the invention in the treatment of major depressive disorder, or predisposition thereto.

Also provided is the use of a substance according to the invention as a medicament.

Yet further provided is the use of a substance according to the invention in the manufacture of a medicament for the treatment of major depressive disorder, or predisposition thereto.

A kit for differentially diagnosing schizophrenia, bipolar disorder or major depressive disorder, or predisposition thereto is provided. A kit for diagnosing or monitoring major depressive disorder, or predisposition thereto is also provided. Suitably a kit according to the invention may contain one or more components selected from the group: a ligand specific for the analyte biomarker or a structural/shape mimic of the analyte biomarker, one or more controls, one or more reagents and one or more consumables; optionally together with instructions for use of the kit in accordance with any of the methods defined herein.

The identification of biomarkers for differentially diagnosing schizophrenia, bipolar disorder or major depressive disorder permits integration of diagnostic procedures and therapeutic regimes. Currently there are significant delays in determining effective treatment and hitherto it has not been possible to perform rapid assessment of drug response. Traditionally, many psychiatric therapies have required treatment trials lasting weeks to months for a given therapeutic approach. Detection of an analyte biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, in a time frame and with precision, not achievable using the current subjective measures.

Furthermore, diagnostic biomarker tests are useful to identify family members or patients at high risk of developing schizophrenia, bipolar disorder or major depressive disorder. This permits initiation of appropriate therapy, or preventive measures, e.g., managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder, poor patient compliance or substance abuse. If pharmacological treatment is assessed to be inadequate, then therapy can be reinstated or increased; a change in therapy can be given if appropriate. As the biomarkers are sensitive to the state of the disorder, they provide an indication of the impact of drug therapy or of substance abuse.

The following studies illustrate the invention.

Example 1

Methodology
(A) Raw Data Acquisition 144 analytes were measured in the serum of 653 patients with schizophrenia (SZ), bipolar disorder (BD) or major depressive disorder (MDD) using multiplexed immunoassays which may be performed in accordance with known procedures. All samples were analyzed in a randomized and blinded manner.

(B) Data Pre-Analysis

Available metadata was investigated to estimate its relationship to the outcome variable of interest (e.g., pair-wise difference between all disease groups) in order to identify potential sources of selection bias. Also, outcome as well as molecular variables were inspected visually and statistically to identify underlying distributions and potential justifications for future data transformation or normalization. The relationship between meta-data and molecular data was examined to identify potential confounding factors and covariates.

(C) Data Processing

Data processing consisted of three steps:
  (i) Missing Value Imputation

Values measured below the lower limit of detection were replaced by half the minimum value measured for a given analyte. Values higher than the upper limit of detection were replaced by the upper limit of detection for a given analyte. Samples with other types of missing values in any of the measured analytes were excluded from further analysis.

(ii) Data Transformation/Normalization

All analytes were normalized to have a mean of 0 and standard deviation of one across all samples.

(iii) Outlier Detection and Removal

No outliers were removed from analysis.

(D) Univariate Analysis

The dataset was split randomly into a training (n=431) and a test set (n=222), stratified by group size. All further analysis except for the validation of multivariate decision rules were performed on the training set. The univariate analysis comprised the application of parametric and non-parametric methods to identify individual analytes that were associated with the outcome. The false discovery rate was determined to estimate potential biological reproducibility of marker candidates. Analysis of Covariance was used to determine the impact of covariates on the association between molecular data and outcome. The output of this analysis is also used to estimate the usefulness of future subgroup analysis (e.g., based on covariate-diagnosis interactions).

(E) Multivariate Analysis

Multivariate analysis using Linear Discriminant Analysis (LDA) was aimed at the identification of analyte combinations that were highly associated with the outcome variable. Group weights for algorithm training were set to be inversely proportional to group size. Stepwise backward elimination starting with the entire set of 144 analytes was then employed to determine the optimal set of analytes. During this procedure, every variable was excluded and performance tested by 10 fold cross-validation and quantified using the overall correctness rate (1—error rate). The procedure was stopped when the removal of additional analytes did not improve the performance. The model found to be optimal was then blindly tested on the test set. This showed that the set of 131 analytes had an optimal accuracy of 97/98 (% sens/spec MDD vs all), 96/99 (% sens/spec SZ vs all) and 97/98 (% sens/spec BD vs all) on the training and 74/89 (% sens/spec MDD vs all), 79/86 (% sens/spec SZ vs all) and 63/88 (% sens/spec BD vs all) on the test set.

(F) Subgroup Analysis

The multivariate decision rules may be supplemented with covariates of interest or the dataset stratified according to co-variates to estimate separate decision rules for each covariate level. The same procedure as described in E) may then be repeated.

Results

Plotting the data in the space of the Linear Discriminants (LD) revealed that LD1 maximized the separation between BD and the remaining two groups (comparison A) whereas LD2 maximized the separation between SZ and the remaining two groups (comparison B). For these comparisons, the individual variable importance on the training set was determined using two tailed Wilcoxon rank sum tests. This showed that 87 variables were significant with p<0.05 for either comparison A or comparison B (see results shown in Table 1 wherein the italicized figures show significant results). A new LDA model was then built in the training set using the 87 analytes only and performance tested blindly on the test set. This showed that the set of 87 analytes had an accuracy of 94/96 (% sens/spec MDD vs all), 83/95 (% sens/spec SZ vs all) and 97/90 (% sens/spec BD vs all) on the training and 72/89 (% sens/spec MDD vs all), 72/88 (% sens/spec SZ vs all) and 69/83 (% sens/spec BD vs all) on the test set.

TABLE 1

Summary of significant findings

| Analyte | P value SZ vs all | P value BD vs all | Fold Change SZ vs all | Fold Change BD vs all |
|---|---|---|---|---|
| Alpha 1 Antitrypsin | 5.39E-13 | 1.12E-06 | 1.191906 | 0.851488 |
| ACTH (Adrenocorticotropic Hormone) | 0.287945967 | 0.0162262 | 0.788944 | 0.242837 |
| AgRP (Agouti related Protein) | 0.681439757 | 0.00238976 | 1.383625 | 0.140767 |
| Apolipoprotein A1 | 0.2688168 | 7.70E-05 | 1.116513 | 0.87022 |
| Apolipoprotein H | 0.01042979 | 0.00116553 | 1.07483 | 1.05084 |
| AXL | 0.023395127 | 0.02578637 | 1.09319 | 0.939709 |
| Betacellulin | 0.221259014 | 0.00043174 | 1.128459 | 0.269441 |
| BLC (B Lymphocyte Chemoattractant) | 0.000128926 | 0.96653899 | 0.708759 | 0.777831 |
| BDNF (Brain Derived Neurotrophic Factor) | 0.118394954 | 0.0023028 | 0.940228 | 1.241597 |
| Complement 3 | 0.000905712 | 8.99E-06 | 1.110187 | 0.847305 |
| Cancer Antigen 125 | 0.016866741 | 0.27518476 | 0.763425 | 0.114207 |
| Carcinoembryonic Antigen | 0.000794176 | 0.83869997 | 1.142391 | 1.473773 |
| CgA (Chromogranin A) | 0.015116318 | 0.14757984 | 1.211252 | 1.174303 |
| Creatine Kinase MB | 0.035854997 | 0.00095055 | 1.377545 | 0.236166 |
| Cortisol | 0.287360538 | 6.98E-05 | 0.600433 | 0.665266 |
| CTGF (Connective Tissue Growth Factor) | 0.073078033 | 2.59E-05 | 1.149584 | 1.036082 |
| EGF R | 0.005595367 | 0.0003375 | 0.814714 | 1.617453 |
| Endothelin 1 | 0.017192072 | 1.92E-10 | 0.784805 | 0.65674 |
| EN RAGE | 0.530734788 | 0.00354996 | 0.906107 | 0.474486 |
| Eotaxin | 0.049103224 | 0.07071163 | 1.01822 | 1.419914 |
| Epiregulin | 0.590619663 | 6.84E-05 | 1.100216 | 0.286547 |
| Erythropoietin | 0.003529247 | 0.15385983 | 0.737062 | 0.111551 |
| Factor VII | 0.000517649 | 0.12647448 | 0.88349 | 0.980132 |
| Fas | 0.03338261 | 0.0035666 | 1.238456 | 0.549023 |
| Fas Ligand | 0.006117649 | 0.41245083 | 0.807907 | 0.573437 |
| Ferritin | 0.025008823 | 0.27985895 | 1.026717 | 1.361225 |
| FGF basic | 7.14E-06 | 0.00167629 | 0.38799 | 1.229554 |
| Fibrinogen | 8.36E-09 | 0.06471408 | 0.685768 | 0.444849 |
| FSH (Follicle Stimulating Hormone) | 0.647996325 | 0.00047166 | 0.745328 | 0.023907 |
| GM CSF | 0.131719457 | 0.00018594 | 0.890562 | 0.460263 |
| GST | 0.235956854 | 0.00045052 | 1.107386 | 0.079517 |
| Haptoglobin | 0.039520758 | 0.02202221 | 1.170138 | 0.372996 |
| HB EGF | 0.740697544 | 9.05E-06 | 1.011785 | 0.452677 |
| HGF (Hepatocyte growth factor) | 1.44E-05 | 0.03887698 | 1.216893 | 0.997123 |
| IFN gamma | 9.73E-06 | 0.51914881 | 0.767239 | 0.387243 |
| Ig A | 0.024256296 | 3.08E-08 | 1.134532 | 0.629851 |
| Ig M | 0.58088978 | 6.10E-08 | 0.948876 | 0.548718 |
| IL 10 | 0.641846738 | 1.28E-06 | 1.046327 | 1.030757 |
| IL 12p70 | 0.035250429 | 5.47E-08 | 0.795202 | 1.456509 |
| IL 13 | 3.89E-05 | 0.03020694 | 1.154051 | 1.37269 |
| IL 15 | 0.279914795 | 0.02219907 | 1.065816 | 1.188576 |
| IL 16 | 0.004885507 | 0.01986419 | 0.901194 | 0.811671 |
| IL 1alpha | 0.28206842 | 0.00052536 | 1.090615 | 0.295168 |
| IL 1beta | 0.01422583 | 2.76E-05 | 0.70782 | 0.7452 |
| IL 1ra | 7.01E-05 | 0.00621744 | 0.833983 | 0.581288 |
| IL 2 | 1.50E-05 | 0.01118656 | 1.3881 | 0.692555 |
| IL 3 | 0.181015815 | 0.00257271 | 0.942968 | 0.478811 |
| IL 4 | 0.050397929 | 1.29E-07 | 0.776577 | 1.844202 |
| IL 5 | 0.008022598 | 0.24284721 | 1.213999 | 1.018676 |
| IL 7 | 0.696312735 | 7.55E-05 | 1.025227 | 1.261315 |
| Leptin | 0.000429207 | 0.08768237 | 0.699186 | 0.531616 |
| LH (Luteinizing Hormone) | 0.678080622 | 0.0001158 | 1.270592 | 0.032703 |
| Lipoprotein a | 0.001404253 | 0.01313601 | 1.245417 | 0.035758 |
| Lymphotactin | 0.662621249 | 0.00036503 | 1.502729 | 0.91463 |
| M CSF | 0.090482487 | 0.00993254 | 0.662795 | 0.390895 |
| MDC | 0.001904362 | 0.04537958 | 1.112031 | 0.703454 |
| MIP 1alpha | 0.78500453 | 0.00049851 | 1.022736 | 0.620704 |
| MIP 1beta | 0.559081337 | 0.020062 | 0.990828 | 0.647195 |
| MMP 3 | 0.002837518 | 0.37518411 | 1.210726 | 1.18633 |

TABLE 1-continued

Summary of significant findings

| Analyte | P value SZ vs all | P value BD vs all | Fold Change SZ vs all | Fold Change BD vs all |
|---|---|---|---|---|
| Myoglobin | 0.015935413 | 0.24062142 | 1.412399 | 1.067797 |
| NrCAM | 0.296296235 | 9.90E-08 | 0.908537 | 1.264092 |
| PAI 1 | 0.002124186 | 0.02349196 | 1.114658 | 0.893033 |
| Prostatic Acid Phosphatase | 0.197064157 | 0.00945003 | 1.069076 | 0.655672 |
| PAPP A | 0.013412218 | 0.22054792 | 0.895577 | 0.393059 |
| PDGF | 0.009425282 | 5.69E-06 | 1.116802 | 0.800418 |
| Prolactin | 0.000630413 | 0.01470168 | 1.529281 | 0.119264 |
| Prostate Specific Antigen Free | 0.00034538 | 0.19734263 | 0.766415 | 2.308312 |
| PARC | 0.060574488 | 0.00286174 | 1.171208 | 0.872718 |
| Peptide YY | 0.030620953 | 0.00435923 | 1.258531 | 0.477843 |
| RANTES | 0.044478405 | 0.50873414 | 1.106707 | 1.463765 |
| Resistin | 0.250604167 | 0.00460714 | 1.074309 | 0.406792 |
| S100b | 3.48E-07 | 0.00298113 | 1.770173 | 0.363992 |
| Serum Amyloid P | 1.13E-08 | 0.09678634 | 1.230749 | 1.035348 |
| SGOT | 0.1254574 | 0.00094291 | 0.896135 | 1.511548 |
| SHBG | 0.640999869 | 0.00506918 | 0.883985 | 0.381151 |
| SOD | 0.393250817 | 0.0003424 | 0.806505 | 1.456165 |
| Thyroxine Binding Globulin | 1.30E-06 | 0.00069872 | 1.167964 | 0.830693 |
| Testosterone | 0.000804886 | 0.01908528 | 1.209673 | 1.320028 |
| Tissue Factor | 0.120412637 | 0.00836277 | 0.947822 | 0.864874 |
| TECK | 0.304442755 | 0.00058749 | 1.174253 | 0.518806 |
| TIMP 1 | 0.001117957 | 0.44479463 | 1.087212 | 1.06027 |
| TNF RII | 4.92E-07 | 0.12407412 | 1.197714 | 0.882536 |
| TRAIL R3 | 0.847829048 | 0.00153575 | 0.963468 | 0.474926 |
| Thyroid Stimulating Hormone | 0.022904874 | 0.03318409 | 0.982925 | 0.56831 |
| TSP 1 | 0.006843535 | 0.01774703 | 0.725802 | 1.026327 |
| VCAM 1 | 0.000277209 | 0.88752154 | 1.097533 | 1.048271 |
| von Willebrand Factor | 0.025486699 | 0.00016956 | 1.236008 | 0.208553 |

FIG. 1 shows the results obtained when the data was subjected to Linear Discriminant Analysis (LDA) wherein the x-axis (LD1) separates primarily bipolar disorder from schizophrenia and major depressive disorder and the y-axis (LD2) separates schizophrenia from bipolar disorder and major depressive disorder. It will be apparent that combination of both LD1 and LD2 provide differential diagnosis between all three groups.

Example 2

This study measured levels of 247 molecules between serum collected from 2 separate cohorts. The first cohort contained 35 major depressive disorder (MDD) patients and 40 well matched controls. The second cohort contained 40 patients suffering from schizophrenia (paranoid subtype (295.30)) all of which were antipsychotic-naive or had been off medication for at least six weeks prior to sample collection and 40 well matched controls. Levels of all molecular analytes were determined using a highly reproducible multiplexed immunoassay platform. The correlation structure between all analytes was assessed to infer potential co-regulation structures.

A panel of 15 markers was found to be significantly altered in the MDD group when compared with the schizophrenia group. These abnormalities remained significant after adjustment for all recorded baseline characteristics including age, sex, body mass index and smoking. Among the significant markers, a highly prominent correlation structure was found.

Methodology

Patients

In the present study, samples were investigated from patients suffering from major depressive disorder (MDD) (n=35), schizophrenia (n=40) and well matched controls (n=40). All individuals were fasted at the time of blood sample collection and featured no co-morbidities. The ethical committees of the medical faculties of the partner universities approved the protocols of this study. Informed consent was given in writing by all participants and clinical investigations were conducted according to the principles expressed in the Declaration of Helsinki.

Sample Preparation

Blood was collected in S-Monovette 7.5 mL serum tubes (Sarstedt), incubated at room temperature for 2 hours to allow for blood coagulation and then centrifuged at 4000×g for 5 minutes. The supernatant was stored at −80° C. in Low Binding Eppendorf tubes.

Assay Methods

A total of 247 analytes were measured using a set of proprietary multiplexed immunoassays (Human MAP) at Rules Based Medicine in their Luminex-based, CLIA-certified laboratory (however measurement could equally be performed using singleton ELISA). Each antigen assay was calibrated using 8-point standard curves conducted in duplicate, and raw intensity measurements were interpreted into final protein concentrations. Machine performance was verified using quality control samples at low, medium, and high levels for each analyte in duplicate. All standard and quality control samples were in a complex plasma-based matrix to match the sample background. The autoimmune and infectious disease assays were qualitative and the results obtained for unknown samples were compared with established cut-off values. Because sera were analyzed at a previously optimized dilution, any sample exceeding the maximum concentration of the calibration curve was arbitrarily assigned the concentration of the highest standard, whereas those assayed below the minimum concentration of the calibration curve were assigned the value 0.0. For analysis, samples were ordered in a manner to avoid any sequential bias due to the presence or absence of disease, patient age, or age of serum sample. Generally, samples alternated between cases and controls.

Statistical Analysis

The distribution of the data was examined using standard statistics to assess the necessity for transformations, the presence of outliers or artefactual findings. Parametric (T-test) and non-parametric (Wilcoxon Rank Sum statistics) univariate methods were applied to identify significant differences of molecular levels between the disease and control groups. A p-value of less than 0.05 was considered as being significant. The False Discovery Rate (FDR) was controlled according to Benjamini et al. (J Roy Statist Soc Ser B. 1995; 57:289-300). Multivariate statistics (Principal Component Analysis, PCA and Partial Least Squares Discriminant Analysis, PLS-DA) were applied to identify potential groups of markers that discriminated patient from control groups and to assess the agreement with univariate methods.

Results

This study investigated levels of 247 molecular analytes in serum from 35 patients suffering from major depressive disorder, 40 patients suffering from schizophrenia and well matched controls (n=40). Demographic details can be found in Table 2:

TABLE 2

Demographic details of patients and healthy volunteers

|  | Healthy Controls | Major Depressive Disorder | Schizophrenia |
|---|---|---|---|
| Number | 40 | 35 | 40 |
| Sex (m/f) | 26/14 | 13/22 | 27/13 |
| Age | 36 ± 11 | 40 ± 14 | 35 ± 10 |

Applying T-tests, levels of 15 analytes were found to be significantly altered between the MDD group and the schizophrenia group (Table 3). These values were in very good agreement with the results obtained from non-parametric and multivariate analyses.

TABLE 3

Summary of significant findings

| Analyte | P - value | Fold change |
|---|---|---|
| Progesterone | 0.003515 | 1.409579 |
| IL-10 | 0.004413 | 1.453919 |
| Brain Derived Neurotrophic Factor (BDNF) | 0.013713 | 0.868194 |
| Serum Amyloid P | 0.014821 | 1.228438 |
| sRAGE | 0.017552 | 0.706543 |
| Betacellulin | 0.018455 | 2.267366 |
| Chromogranin A | 0.022812 | 1.914507 |
| Creatine Kinase MB | 0.024868 | 1.994627 |
| IGF-1 | 0.02641 | 0.615415 |
| MIP-3 alpha | 0.026793 | 1.591807 |
| S100b | 0.031904 | 1.498588 |
| MMP-3 | 0.034074 | 1.390886 |
| IL-1ra | 0.035272 | 1.289866 |
| Tamm-Horsfall Protein (THP) | 0.036211 | 1.348363 |
| IL-18 | 0.041492 | 1.209558 |

In particular, two analytes (MMP-3 and IL-1ra) were also found to be significantly altered between MDD patients and healthy controls within the MDD cohort (Table 4).

TABLE 4

Summary of significant findings

| Analyte | P - value | Fold change |
|---|---|---|
| MMP-3 | 0.041043439 | 0.745898954 |
| IL-1ra | 0.006801532 | 1.334898635 |

The invention claimed is:

1. A method for treating an individual with an antipsychotic agent, wherein the individual is suffering from or having a predisposition for either schizophrenia or bipolar disorder or major depressive disorder, comprising:
  a) obtaining a biological sample from the individual;
  b) quantifying concentrations of a panel of biomarkers in the biological sample by subjecting the sample to SELDI (-TOF) spectrometry, MALOI (-TOF) spectrometry, a 1-D gel-based analysis, a 2-D gel-based analysis, mass spectrometry (MS), liquid chromatography (LC), reverse phase liquid chromatography (RP-LC), size permeation chromatography, gel filtration chromatography, ion exchange chromatography, affinity chromatography, FPLC, HPLC, UPLC, other LC-based techniques, other LC-MS-based technique, or combinations thereof, or
  by using an immunological method, a biosensor method, a microanalytical method, a microengineered method, a microseparation method, an immunochromatography method, or combinations thereof;
c) generating a biomarker profile from the concentrations of the panel of biomarkers of the individual, wherein the panel of biomarkers comprises 5 to 15 biomarkers and wherein the panel of biomarkers comprises the analytes MMP-3, Alpha 1 Antitrypsin and Serum Amyloid P;
d) determining that the biomarker profile of the individual has a statistically significant similarity with either one of a biomarker profile obtained from subjects with schizophrenia, subjects with bipolar disorder, or subjects with major depressive disorder; and
e) diagnosing the individual as suffering from or having a predisposition for either schizophrenia or bipolar disorder or major depressive disorder based at least in part on the statistically significant similarity of the biomarker profile of the individual to the biomarker profile of subjects with either schizophrenia, bipolar disorder or major depressive disorder; and
f) administering an antipsychotic agent to the individual identified as suffering from or having a predisposition for either schizophrenia or bipolar disorder or major depressive disorder.

2. The method of claim 1, wherein the panel of biomarkers further comprises one or more analytes selected from Apolipoprotein A1, Apolipoprotein H, AXL, BDNF (Brain Derived Neurotrophic Factor), Betacellulin, Complement 3, CgA (Chromogranin A), Creatine Kinase MB, EGF R, Endothelin 1, Fas, FGF basic, Haptoglobin, HGF (Hepatocyte growth factor), Ig A, IL-1ra, IL 12p70, IL 10, IL 13, IL 16, IL 1beta, IL 2, Lipoprotein a, MDC,-PAI 1, PDGF, Prolactin, Peptide YY, S100b, Thyroxine Binding Globulin, Testosterone, Thyroid Stimulating Hormone, TSP 1, and von Willebrand Factor.

3. The method of claim 2, wherein the panel of biomarkers further comprises one or more analytes selected from ACTH (Adrenocorticotropic Hormone), AgRP (Agouti related Protein), BLC (B Lymphocyte Chemoattractant), Cancer Antigen 125, Carcinoembryonic Antigen, Cortisol, CTGF (Connective Tissue Growth Factor), EN RAGE, Eotaxin, Epiregulin, Erythropoietin, Factor VII, Fas Ligand, Ferritin, Fibrinogen, FSH (Follicle Stimulating Hormone), GM CSF, GST, HB EGF, IFN gamma, IGF-1, Ig M, IL 15, IL 18, IL 1alpha, IL 3, IL 4, IL 5, IL 7, Leptin, LH (Luteinizing Hormone), Lymphotactin, M CSF, MIP 1 alpha, MIP 3 alpha, MIP 1 beta, Myoglobin, NrCAM, Prostatic Acid Phosphatase, PAPPA, Progesterone, Prostate Specific Antigen Free, PARC, RANTES, Resistin, SGOT, SHBG, SOD, sRAGE, Tamm-Horsfall Protein (THP), Tissue Factor, TECK, TIMP 1, TNF RII, TRAIL R3, and VCAM 1.

4. The method of claim 1, wherein the biological sample comprises cerebrospinal fluid, whole blood, blood serum, plasma, urine, saliva, other bodily fluid, breath, condensed breath, or an extract, purification, or dilution of any of these.

5. The method of claim 1, wherein one or more of the biomarkers may be replaced by a molecule, or a measurable fragment of the molecule, found upstream or downstream of the biomarker in a biological pathway.

6. A method for treating an individual with an antipsychotic agent, wherein the individual is suffering from major depressive disorder or schizophrenia, comprising:
a) obtaining a biological sample of an individual;
b) quantifying concentrations of a panel of biomarkers in the biological sample by subjecting the sample to SELDI (-TOF) spectrometry, MALDI (-TOF) spectrometry, a 1-D gel-based analysis, a 2-D gel-based analysis, mass spectrometry (MS), liquid chromatography (LC), reverse phase liquid chromatography (RP-LC), size permeation chromatography, gel filtration chromatography, ion exchange chromatography, affinity chromatography, FPLC, HPLC, UPLC, other LC-based techniques, other LC-MS-based technique, or combinations thereof or
by using an immunological method, a biosensor method, a microanalytical method, a microengineered method, a microseparation method, an immunochromatography method, or combinations thereof;
c) generating a biomarker profile from the concentrations of the panel of biomarkers of the individual, wherein the panel of biomarkers comprises 5 to 15 biomarkers and wherein the panel of biomarkers comprises MMP-3, Alpha 1 Antitrypsin and Serum Amyloid P;
d) determining that the biomarker profile of the individual has a statistically significant similarity with either one of a biomarker profile obtained from subjects with schizophrenia, or subjects with major depressive disorder; and
e) diagnosing the individual as suffering from or having a predisposition for either schizophrenia or major depressive disorder based at least in part on the statistically significant similarity of the biomarker profile of the individual to the biomarker profile of subjects with either schizophrenia or major depressive disorder; and
f) administering an antipsychotic agent to the individual identified as suffering from major depressive disorder or schizophrenia.

7. The method of claim 6, wherein the panel of biomarkers further comprises one or more analytes selected from Apolipoprotein A1, progesterone, IL-10, BDNF (Brain Derived Neurotrophic Factor), sRAGE, Betacellulin, CgA (Chromogranin A), Creatine Kinase MB, IGF-1, MIP 3 alpha, S100b, IL-1ra, Tamm-Horsfall Protein (THP), and IL 18.

8. The method of claim 6, wherein the biological sample comprises cerebrospinal fluid, whole blood, blood serum, plasma, urine, saliva, other bodily fluid, breath, condensed breath, or an extract, purification, or dilution of any of these.

9. The method of claim 6, wherein one or more of the biomarkers may be replaced by a molecule, or a measurable fragment of the molecule, found upstream or downstream of the biomarker in a biological pathway.

10. A method of treating an individual suspected of suffering from schizophrenia, bipolar disorder, or major depressive disorder or a predisposition thereto, comprising:
a) obtaining a biological sample of an individual;
b) quantifying concentrations of a panel of biomarkers in the biological sample;
c) generating a biomarker profile from the concentrations of the panel of biomarkers of the individual;
d) determining that the biomarker profile of the individual has a statistically significant similarity with either one of a biomarker profile obtained from subjects with schizophrenia, subjects with bipolar disorder, or subjects with major depressive disorder;
e) differentially diagnosing the individual as suffering from or having a predisposition for either schizophrenia or bipolar disorder or major depressive disorder based at least in part on the statistically significant similarity of the biomarker profile of the individual to the biomarker profile of subjects with either schizophrenia, bipolar disorder or major depressive disorder, wherein the panel of biomarkers comprises 5 to 15 biomarkers and wherein the panel of biomarkers comprises the analytes MMP-3, Alpha 1 Antitrypsin and Serum Amyloid P;

f) customizing a treatment regimen for the individual based at least in part on the differential diagnosis; and g) effectuating the treatment regimen in the individual differentially diagnosed as suffering from or having a predisposition for either schizophrenia or biopolar disorder or major depressive disorder wherein the individual is administered an antipsychotic agent.

11. The method of claim 10, wherein the panel of biomarkers further comprises one or more analytes selected from Apolipoprotein A1, Apolipoprotein H, AXL, BDNF (Brain Derived Neurotrophic Factor), Betacellulin, Complement 3, CgA (Chromogranin A), Creatine Kinase MB, EGF R, Endothelin 1, Fas, FGF basic, Haptoglobin, HGF (Hepatocyte growth factor), Ig A, IL-1ra, IL 12p70, IL 10, IL 13, IL 16, IL 1beta, IL 2, Lipoprotein a, MDC, PAI 1, PDGF, Prolactin, Peptide YY, S100b, Thyroxine Binding Globulin, Testosterone, Thyroid Stimulating Hormone, TSP 1, and von Willebrand Factor.

12. The method of claim 11, wherein the panel of biomarkers further comprises one or more analytes selected from ACTH (Adrenocorticotropic Hormone), AgRP (Agouti related Protein), BLC (B Lymphocyte Chemoattractant), Cancer Antigen 125, Carcinoembryonic Antigen, Cortisol, CTGF (Connective Tissue Growth Factor), EN RAGE, Eotaxin, Epiregulin, Erythropoietin, Factor VII, Fas Ligand, Ferritin, Fibrinogen, FSH (Follicle Stimulating Hormone), GM CSF, GST, HB EGF, IFN gamma, IGF-1, Ig M, IL 15, IL 18, IL 1 alpha, IL 3, IL 4, IL 5, IL 7, Leptin, LH (Luteinizing Hormone), Lymphotactin, M CSF, MIP 1 alpha, MIP 3 alpha, MIP 1 beta, Myoglobin, NrCAM, Prostatic Acid Phosphatase, PAPPA, Progesterone, Prostate Specific Antigen Free, PARC, RANTES, Resistin, SGOT, SHBG, SOD, sRAGE, Tamm-Horsfall Protein (THP), Tissue Factor, TECK, TIMP 1, TNF RII, TRAIL R3, and VCAM 1.

13. The method of claim 12, wherein the treatment regimen is further customized based at least in part on whether there is a statistically significant similarity or difference between the individual's biomarker profiles generated on two or more occasions.

14. The method of claim 13, wherein biomarker profiles from the individual are generated prior to commencement of the treatment regimen, and/or at an earlier stage of the treatment regimen.

15. The method of claim 13, wherein biomarker profiles from the individual are generated at intervals throughout the individual's lifetime.

16. The method of claim 12, wherein customizing the treatment regimen further comprises one or more selections of therapy selected from: type and/or dosing of medications, type and/or duration of psychotherapy, type and/or duration of counseling, type and/or duration of hospitalization, type and/or dosing of electroconvulsive therapy.

* * * * *